(12) United States Patent
Widmann

(10) Patent No.: US 7,694,807 B2
(45) Date of Patent: Apr. 13, 2010

(54) DIAPER BUDDY

(76) Inventor: Loretta Plunkett Widmann, 4323 Windswept La., Grapevine, TX (US) 76051

( * ) Notice: Subject to any disclaimer, the term of this patent is extended or adjusted under 35 U.S.C. 154(b) by 304 days.

(21) Appl. No.: 11/730,586

(22) Filed: Apr. 3, 2007

(65) Prior Publication Data

US 2008/0244833 A1 Oct. 9, 2008

(51) Int. Cl.
*A61H 35/00* (2006.01)
(52) U.S. Cl. .................. 206/233; 206/576; 206/825
(58) Field of Classification Search .............. 206/576, 206/581, 233, 229, 823, 494, 805, 825, 278, 206/389, 204, 207, 210
See application file for complete search history.

(56) References Cited

U.S. PATENT DOCUMENTS

| | | | | |
|---|---|---|---|---|
| 3,061,136 | A * | 10/1962 | Sterngart | 220/504 |
| 3,307,687 | A | 3/1967 | Steinman | |
| 4,280,811 | A * | 7/1981 | Howe, Jr. | 493/386 |
| 4,685,559 | A | 8/1987 | Titus | |
| 4,686,745 | A * | 8/1987 | Butler | 24/17 B |
| 5,487,466 | A * | 1/1996 | Robson | 206/214 |
| 5,638,957 | A | 6/1997 | Brasier | |
| 5,868,227 | A | 2/1999 | Garcia | |
| 6,386,776 | B2 * | 5/2002 | Scariano | 401/8 |
| 6,540,084 | B2 * | 4/2003 | Silvers | 206/581 |
| 6,886,693 | B1 | 5/2005 | Davenport et al. | |
| 2005/0143706 | A1 | 6/2005 | Snell | |
| 2006/0283731 | A1 | 12/2006 | De-Vries | |

OTHER PUBLICATIONS

Web Page Showing Regalo Diaper Changing System on Sale Feb. 21, 2007.

* cited by examiner

*Primary Examiner*—Ehud Gartenberg
*Assistant Examiner*—King M Chu
(74) *Attorney, Agent, or Firm*—Stephen R. Greiner

(57) ABSTRACT

A diaper buddy including a container with a base plate. A first side wall is affixed to, and extends downwardly from, the base plate. The first side wall has a closed outline defining the plan of a first compartment for holding a plurality of baby wipes. A first lid is hingedly attached to the first side wall for closing the first compartment. A second side wall is affixed to, and extends upwardly from, the base plate. The second side wall has a closed outline defining the plan of a second compartment for holding a tube of ointment. A second lid is hingedly attached to the second side wall for closing the second compartment. A third side wall is affixed to, and extends upwardly from, the base plate. The third side wall is positioned adjacent to the second side wall, outside the second compartment. The third side wall has a closed outline defining the plan of a third compartment for holding a roll of plastic bags. A third lid is hingedly attached to the third side wall for closing the third compartment. An elastomeric band has opposed ends that are affixed to the base wall between the second compartment and the third compartment for securing a plurality of disposable diapers to the container.

1 Claim, 5 Drawing Sheets

DIAPER BUDDY

FIELD OF THE INVENTION

The present invention relates generally to special receptacles and packages including tissue dispensing means.

BACKGROUND OF THE INVENTION

Changing diapers has never been fun, but it is simple. First, a baby is positioned, face up, upon a changing table or other supporting surface. Then, the retaining tabs of the baby's soiled diaper are unfastened. Next, the baby's buttocks are elevated by raising the baby's feet and any fecal matter on the baby is wiped away with a clean portion of the soiled diaper. Afterward, the soiled diaper is closed and placed in a plastic bag for disposal. Now, the baby's genitals and buttocks are cleaned from front to back with premoistened wipes. Then, the baby's buttocks are lowered onto an open, clean diaper. At this time, the genitals and buttocks can be dried with a towel and a light application of powdered cornstarch. Also, if needed, diaper-rash cream can be applied to irritated skin. Now, the back of the clean diaper is positioned above the waist of the baby to prevent leaks and the front of the diaper is positioned opposite the back. Finally, the retaining tabs of the clean diaper are brought around from the back of the diaper and fastened to the front thereby securing the clean diaper upon the baby. The entire process requires just a few minutes to complete.

When away from home, most caregivers of babies tote the items needed to change diapers in a diaper bag. A diaper bag normally resembles a large purse with numerous interior and exterior pockets. Into these pockets can be positioned: two to four clean diapers, premoistened wipes, cream, powder, plastic bags for containing soiled diapers, washcloths, toys, extra clothing, bottled formula, and medications. So that the "basics" are not inadvertently left behind, some caregivers keep their diaper bags adjacent their front doors or in their cars.

Over time, diaper bags have been improved. For example, some manufacturers have added shoulder straps so that their bags can be carried like a backpack or can be placed over the handles of a stroller. Others offer diaper bags that are compact in size so that a caregiver need not rummage around in massive pockets to find items in a crisis situation. Still others provide bags made with washable fabrics. Nonetheless, many women find diaper bags to be a lot to carry around on anything but the longest outings and prefer to carry: one or two diapers, diaper rash cream, and some wipes in their purses.

SUMMARY OF THE INVENTION

In light of the problems associated with the changing of diapers away from home, it is a principal object of the invention to provide a product, hereinafter a "diaper buddy," of compact size that holds and dispenses diapers, premoistened wipes, diaper rash cream, and bags for containing soiled diapers. The diaper buddy eliminates clutter and keeps away-from-home changing areas neatly organized. The diaper buddy can be used practically anywhere and always keeps diaper changing essentials from becoming lost and within easy reach.

It is an object of the invention to provide improved features and arrangements thereof in a diaper buddy for the purposes described that is compact in size, lightweight in construction, inexpensive to manufacture, and dependable in use.

The foregoing and other objects, features, and advantages of the present invention will become readily apparent upon further review of the following detailed description of the diaper buddy illustrated in the accompanying drawings.

BRIEF DESCRIPTION OF THE DRAWINGS

The present invention may be more readily described with reference to the accompanying drawings, in which.

Similar reference characters denote corresponding features consistently throughout the accompanying drawings.

DETAILED DESCRIPTION OF THE PREFERRED EMBODIMENT

Figure 1:
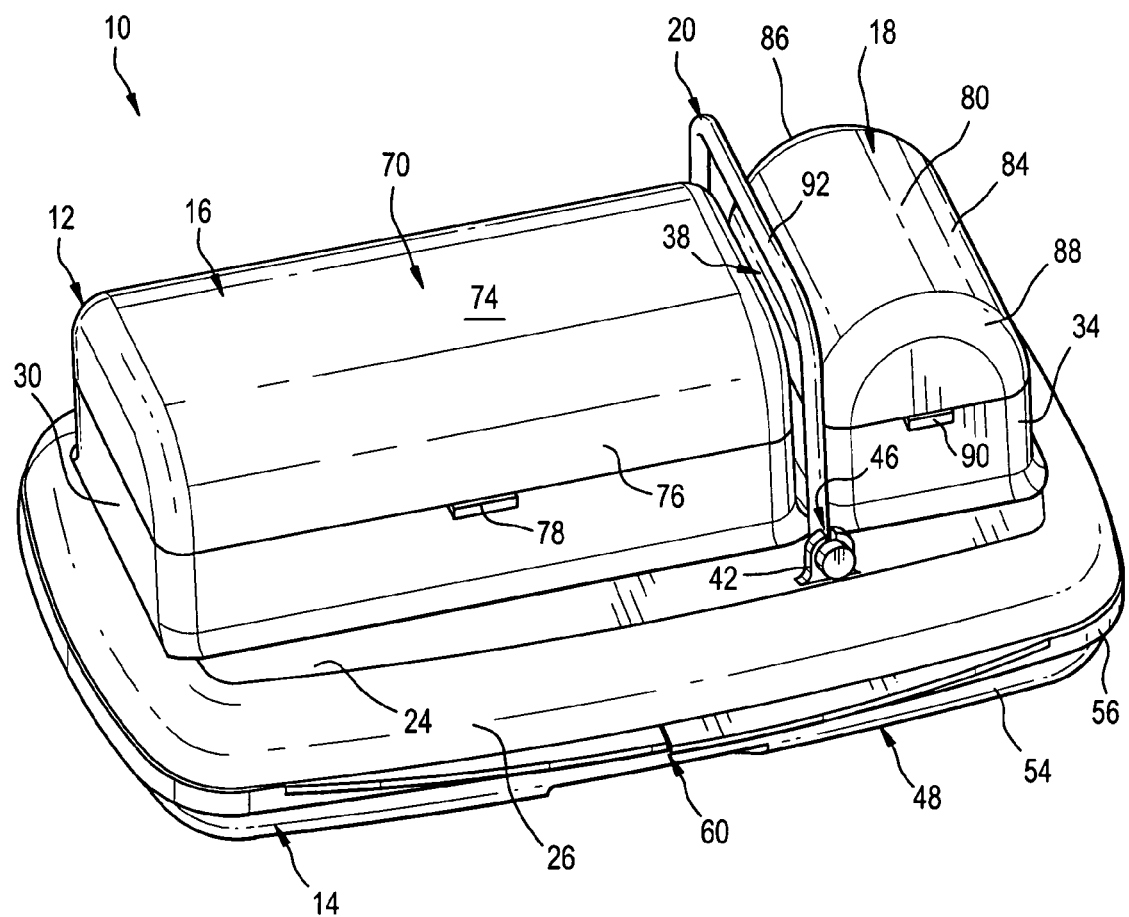
FIG. 1 is a top perspective view of a diaper buddy.
Figure 2:
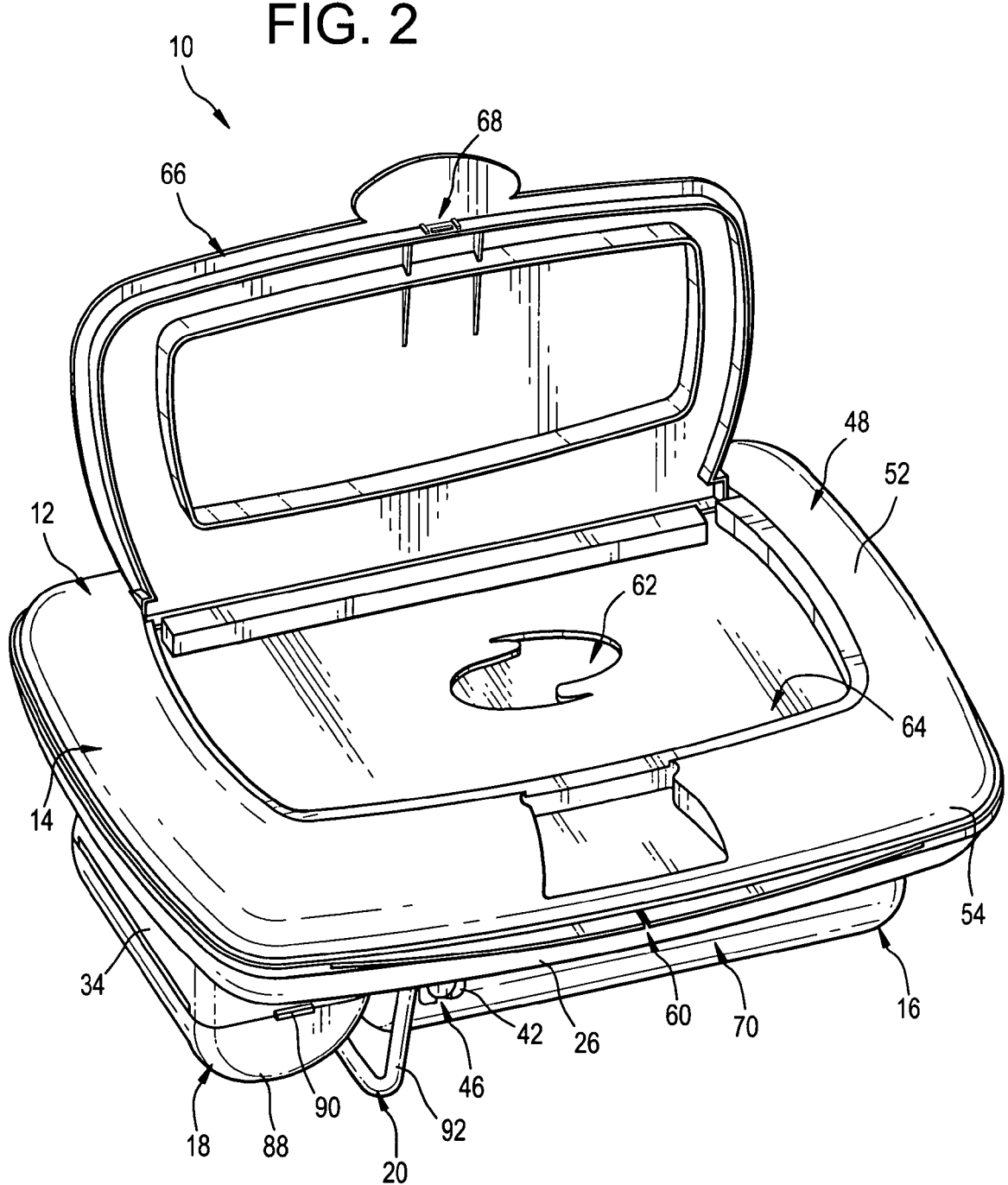
FIG. 2 is a bottom perspective view of the diaper buddy of FIG. 1 with its sealing cover in an open condition so as to reveal interior details thereof.
Figure 3:
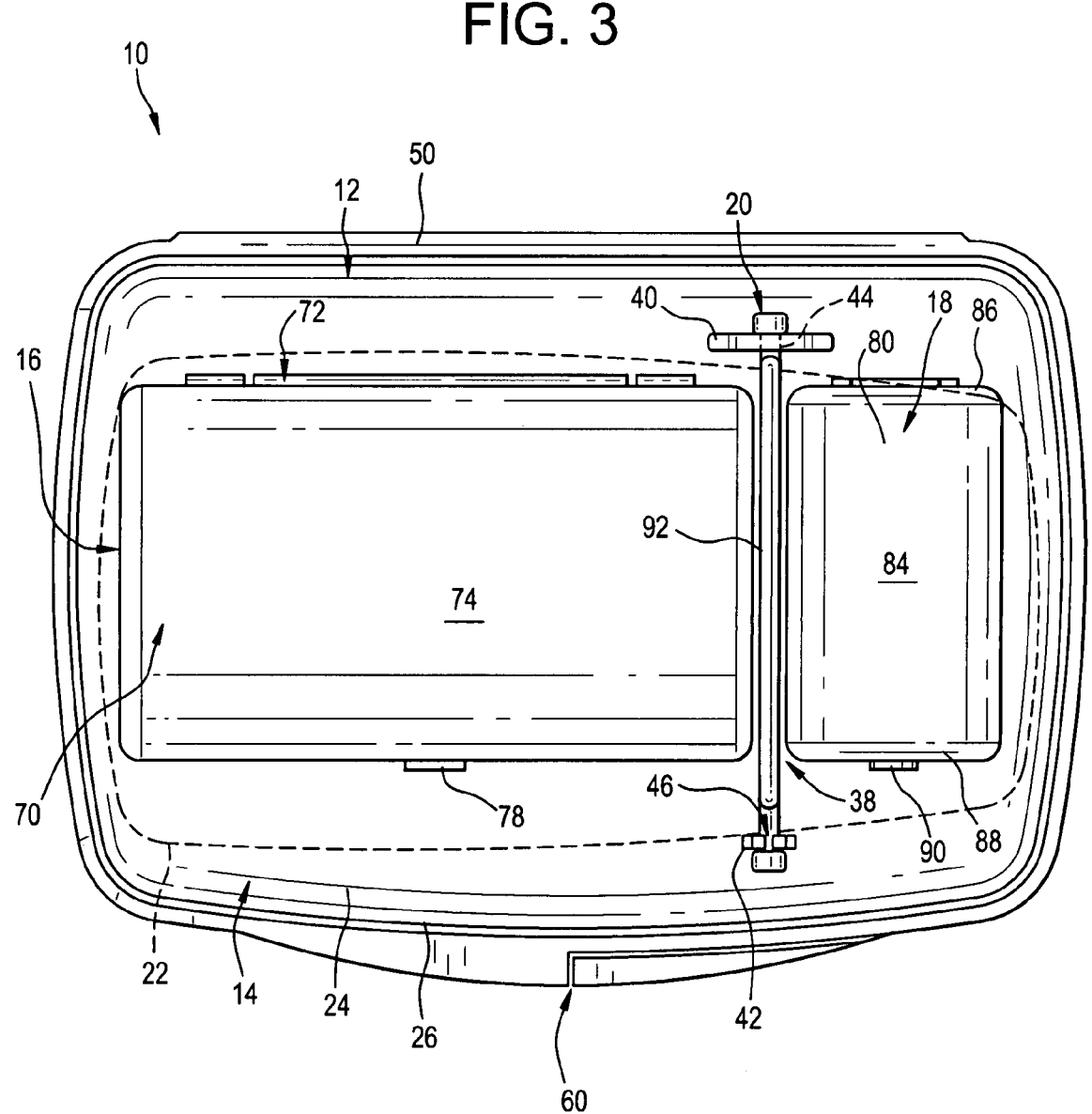
FIG. 3 is a top view of the diaper buddy.
Figure 4:
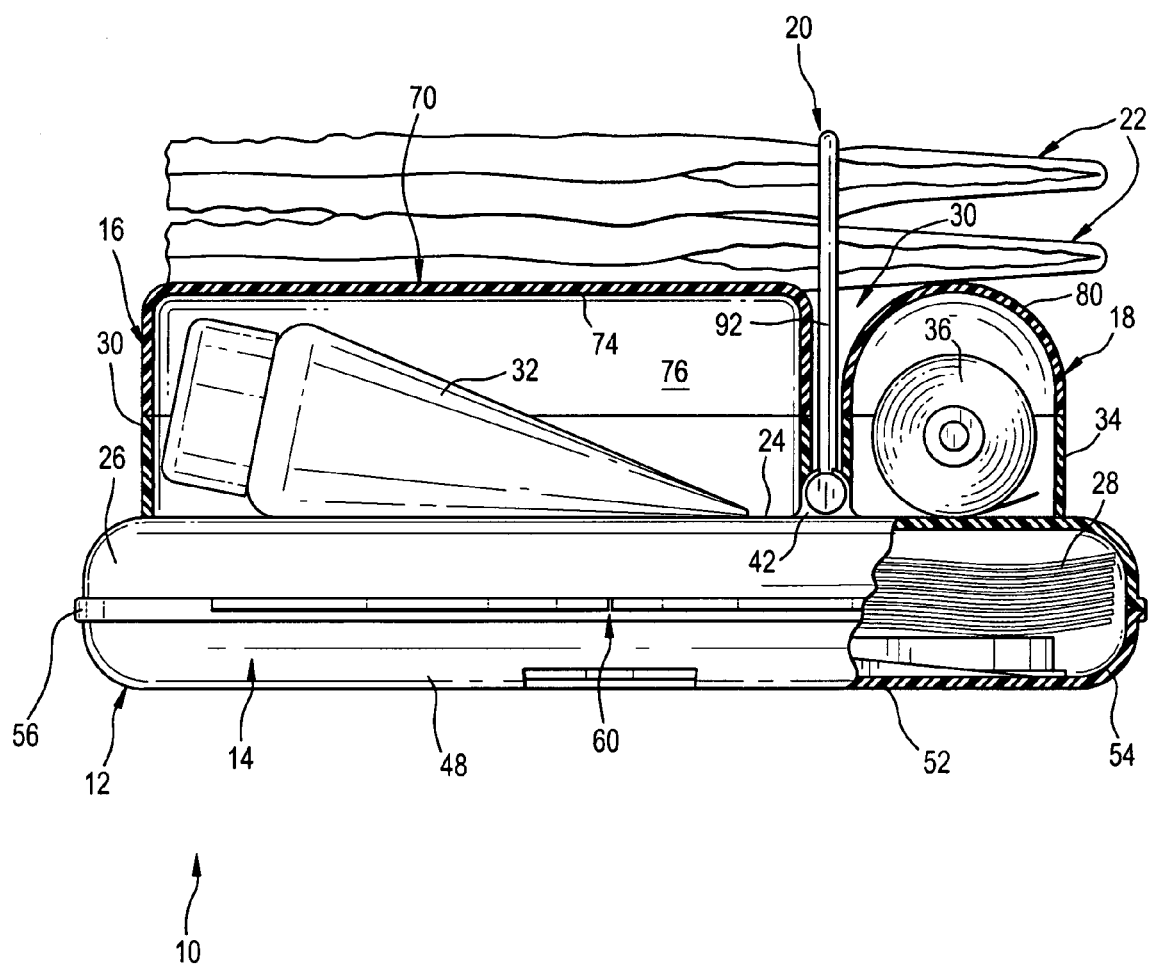
FIG. 4 is a side view of the diaper buddy in a filled condition and with portions broken away to reveal details thereof.
Figure 5:
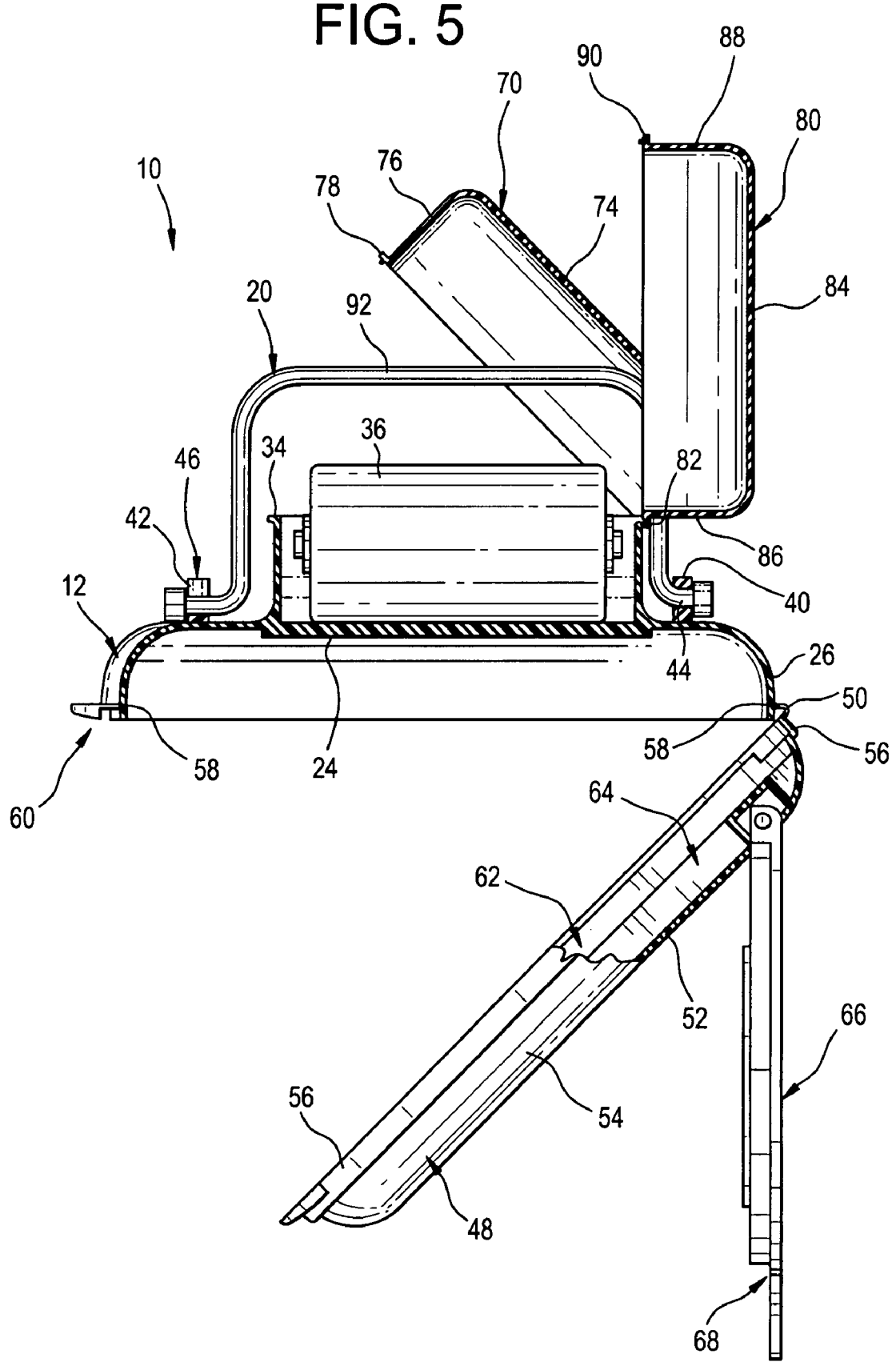
FIG. 5 is a side elevational view of the diaper buddy with its in an open condition and parts broken away to reveal details thereof.

Referring now to the FIGS., a diaper buddy in accordance with the present invention is shown at 10. Diaper buddy 10 has a container 12 with three compartments 14, 16, and 18, the interiors of which can be accessed independently. An elastomeric band 20 is connected to container 12 between compartments 16 and 18 for releasably fastening one or more clean, disposable diapers 22 to container 12.

Container 12 has a base plate 24 of rectangular form that serves as the top of compartment 14 and the bottom of compartments 16 and 18. A first side wall 26 projects downwardly and outwardly from the periphery of base plate 24. As shown, side wall 26 is dimensioned so as to encircle a stack of about one dozen, premoistened wipes 28.

A second side wall 30 projects upwardly from the top of base plate 24 and serves to define the sides of compartment 16. Second side wall 30 is rectangular in outline and is spaced away from first side wall 26. Second side wall 30 has a height that is substantially the same as that of first side wall 26 and is dimensioned to encircle a tube of diaper rash cream 32.

A third side wall 34 projects upwardly from the top of base plate 24 adjacent second side wall 30 and serves to define the sides of compartment 18. Third side wall 34 is rectangular in outline and is spaced a short distance from both first side wall 26 and second side wall 30. Third side wall 34 has a height and a width that are equal to that of second side wall 30 but a length that is ⅓ as great so as to snugly encircle a roll of folded plastic bags 36.

A gap 38 is provided between second side wall 30 and third side wall 34. Affixed to base plate 24, at opposite ends of gap 38, is a pair of elastomeric band retainers 40 and 42. Retainer 40 comprises an upright tab with a hole 44 at its center through which elastomeric band 20 is extended. Retainer 42, however, is an upright tab having a keyhole slot 46 in its top for releasably grasping elastomeric band 20.

A first lid 48 is movably attached to first side wall 26 by means of a hinge 50 and serves as the bottom of compartment 14. Lid 48 has a bottom plate 52 substantially identical in outline to that of base plate 24 and peripheral lip 54 extending upwardly and outwardly from the periphery of bottom plate 52 to engage side wall 26. As shown, lip 54 has a raised edge 56 along its length that forms a seal that keeps wipes 28 moist when edge 56 is pressed against a similar edge 58 along the length of side wall 26 when lid 48 is closed. Hinge 50 is a thin strip of molded plastic that integrally connects the back of lip 54 to the back of side wall 26. A latch 60 with male and female members associated, respectively, with lip 54 and side wall 26 retain lid 48 in a closed configuration beneath side wall 26 until lightly pulled open.

Lid 48 is provided with an opening 62 at its center through which wipes 28 can be withdrawn, one-by-one, from compartment 14. Opening 62 has an S-shape that assists in unfolding wipes 28 as they move from the interior of compartment 14, where they are kept in a folded and interlaced condition prior to use, to the exterior of compartment 14 for use. A recess 64 in bottom plate 52 surrounds opening 62 and collects any liquid that may run from a wipe 28 drawn through opening 62. A sealing cover 66 is hingedly fitted within recess 64 for selectively closing opening 62 so as to prevent the drying of wipes 28 in compartment 14 and to prevent the runoff of liquid from recess 64. A latch 68, with male and female members associated, respectively, with cover 66 and peripheral lip 54, retains cover 66 in a closed configuration within recess 64 until lightly pulled.

A second lid 70 is movably attached to second side wall 30 by means of a hinge 72 and serves as the top of compartment 16. Lid 70 has a rectangular top plate 74 with a peripheral lip 76 that extends downwardly therefrom. Hinge 72 has male and female components associated, respectively, with the back of lip 76 and side wall 30 that permit lid 70 to pivot when the front of lid 70 is selectively elevated. A latch 78 with male and female members associated, respectively, with lip 76 and side wall 30 retain lid 70 in a normally closed configuration atop side wall 30.

A third lid 80 is movably attached to third side wall 34 by means of a hinge 82 and serves as the top of compartment 18. Lid 80 has a cover plate 84 with a cross section resembling that of an inverted "U". Lid 80 also has a pair of end walls 86 and 88 of semi-circular outline that close the front and rear ends of cover plate 84. Hinge 82 has male and female components associated, respectively, with end wall 86 and side wall 34 that permit lid 80 to pivot when the front of lid 80 is elevated. A latch 90 with male and female members associated, respectively, with end wall 88 and side wall 34 retain lid 80 in a normally closed configuration atop side wall 34.

Elastomeric band 20 is formed of natural or synthetic rubber and extends between retainers 40 and 42. Band 20 has an elongated strip 92 whose relaxed length is sufficient to reach up and over gap 38. Strip 92 has a diameter sufficient to permit such to extend through hole 44 in retainer 40 and snap fit into keyhole slot 46 in retainer 42. One of a pair of identical, enlarged heads 94 is formed at each of the opposite ends of strip 92. Each head 94 has a diameter greater than that of strip 92 and large enough to prevent its passage through keyhole slot 46. Further, each head 94 is small enough to pass through hole 44 when compressed upon installation yet large enough to prevent passage through hole 44 during normal use of diaper buddy 10.

The use of diaper buddy 10 is straightforward. First, with diaper buddy 10 being empty, compartment 14 is filled with a dozen wipes 28. This is accomplished by unfastening latch 60 with a light push, opening lid 48, placing a stack of pre-folded, stacked, and premoistened wipes 28 within the confines of side wall 26 and re-closing lid 48. Next, a tube of diaper rash cream 32 is placed within compartment 16 by unfastening latch 78, opening lid 70, positioning tube 32 within the confines of side wall 30 and closing lid 70 again. Now, latch 90 is unfastened. Lid 80 is opened. Roll of plastic bags 36 is placed in compartment 18 by positioning such within the space bounded by side wall 34. And, lid 80 is re-closed. Finally, two or three, clean diapers 22 are slipped under strip 92 of band 20 that is stretched upwardly to accommodate diapers 22. When strip 92 is released, diapers 22 are pulled partially into gap 38 which prevents diapers 22 from sliding atop diaper buddy 10.

With diaper buddy 10 in a fully charged state, it can be carried by itself or it can be slipped into a: purse, suitcase, backpack, or similar enclosure for ready access. During a diaper change, a plastic bag can be unwound from roll 36 in compartment 18 and opened to receive a soiled diaper removed from a baby for convenient disposal. Once the soiled diaper is removed, the baby can be cleaned with one or more wipes 28 drawn from compartment 14 through opening 62. If the baby presents a rash, the rash can be treated with cream 32 withdrawn from compartment 14. Afterward, a clean diaper 22, pulled from beneath strip 92, is affixed to the baby to complete the diaper change.

A diaper change requires just a few minutes to complete with diaper buddy. All the necessary changing supplies, diapers 22, wipes 28, plastic bags 36, and cream 32, are held close at hand by diaper buddy 10. With diaper buddy 10, a caregiver of a baby will never have to hunt for lost supplies in the middle of a diaper change. If diaper buddy 10 is kept filled with changing supplies, it is always ready for immediate use.

While diaper buddy 10 has been described with a high degree of particularity, it will be appreciated by those skilled in the art that modifications can be made to it. Therefore, it is to be understood that the present invention is not limited merely to diaper buddy 10 described above, but encompasses any and all products within the scope of the following claims.

I claim:

1. A diaper buddy, comprising:
   a container including:
      a base plate;
      a first side wall being affixed to, and extending downwardly from, said base plate, said first side wall having a first, closed outline defining the plan of a first compartment for holding a plurality of baby wipes;
      a first lid being hingedly attached to said first side wall for closing said first compartment;
      a second side wall being affixed to, and extending upwardly from, said base plate, said second side wall having a second, closed outline defining the plan of a second compartment for holding a tube of ointment;
      a second lid being hingedly attached to said second side wall for closing said second compartment;
      a third side wall being affixed to, and extending upwardly from, said base plate, said third side wall being positioned adjacent to said second side wall outside said second compartment, said third side wall having a third, closed outline defining the plan of a third compartment for holding a roll of plastic bags;
      a third lid being hingedly attached to said third side wall for closing said third compartment; and,
   an elastomeric band affixed having opposed ends affixed to said base plate between said second compartment and said third compartment.

* * * * *